United States Patent
Tham

(10) Patent No.: US 8,770,191 B2
(45) Date of Patent: Jul. 8, 2014

(54) SYSTEM AND METHOD FOR PROVIDING MECHANICAL VENTILATION SUPPORT TO A PATIENT

(75) Inventor: Robert Q. Tham, Middleton, WI (US)

(73) Assignee: General Electric Company, Schenectady, NY (US)

( * ) Notice: Subject to any disclaimer, the term of this patent is extended or adjusted under 35 U.S.C. 154(b) by 782 days.

(21) Appl. No.: 12/986,782

(22) Filed: Jan. 7, 2011

(65) Prior Publication Data

US 2012/0174925 A1 Jul. 12, 2012

(51) Int. Cl.
*F16K 31/02* (2006.01)
*A62B 9/02* (2006.01)
*A61M 16/00* (2006.01)
*A61M 16/12* (2006.01)
*A61M 16/08* (2006.01)
*A61M 16/01* (2006.01)
*A61M 16/10* (2006.01)
*A61M 16/22* (2006.01)

(52) U.S. Cl.
CPC .......... *A61M 16/01* (2013.01); *A61M 16/0081* (2014.02); *A61M 2016/0015* (2013.01); *A61M 2016/0027* (2013.01); *A61M 16/0075* (2013.01); *A61M 2016/0039* (2013.01); *A61M 16/0051* (2013.01); *A61M 2205/52* (2013.01); *A61M 16/12* (2013.01); *A61M 2016/1025* (2013.01); *A61M 16/1015* (2014.02); *A61M 16/0891* (2014.02); *A61M 16/08* (2013.01); *A61M 2205/50* (2013.01); *A61M 16/22* (2013.01); *A61M 2230/435* (2013.01); *A61M 2016/0042* (2013.01)
USPC .................................. 128/204.21; 128/205.24

(58) Field of Classification Search
USPC ............. 128/204.18, 204.21–204.23, 204.26, 128/204.28, 205.11–205.13, 205.17, 205.24
See application file for complete search history.

(56) References Cited

U.S. PATENT DOCUMENTS 4,266,573 A   5/1981  Braatz
6,041,777 A   3/2000  Faithfull et al.
(Continued)

FOREIGN PATENT DOCUMENTS

EP   0916357 A2   5/1999
GB   1008520 A   10/1965

OTHER PUBLICATIONS

Datex-Ohmeda Anesthesia Delivery Unit; User's Reference Manual; Document No. 8501700-2; Mar. 23, 2003.

(Continued)

*Primary Examiner* — Rachel Young
(74) *Attorney, Agent, or Firm* — Andrus Intellectual Property Law, LLP

(57) ABSTRACT

A system for providing mechanical ventilation support to a patient and includes a mechanical ventilator. A breathing circuit is pneumatically connected between the mechanical ventilator and a patient connection. An inspiratory check valve is disposed within an inspiratory limb of the breathing circuit. A fresh gas manifold provides fresh gas to the breathing circuit for delivery to the patient. A fresh gas valve is disposed between the fresh gas manifold and the breathing circuit. The fresh gas valve is operable between a first position which directs fresh gas upstream of the inspiratory check valve and a second position that directs fresh gas downstream of the inspiratory check valve. A digital signal processor operates the fresh gas valve selectively between the first position and the second position. A method of ventilating a patient includes introducing a flow of fresh gas into an inspiratory limb of the breathing circuit. A ventilatory support value is sensed with at least one sensor disposed within the breathing circuit. An operational condition of the breathing circuit is identified with a digital signal processor. A fresh gas valve is operated with the digital processor between a first position that directs fresh gas to the inspiratory limb upstream from the inspiratory check valve and a second position that directs the fresh gas downstream from the inspiratory check valve.

20 Claims, 6 Drawing Sheets

(56) References Cited

U.S. PATENT DOCUMENTS

| | | |
|---|---|---|
| 6,619,289 B1 | 9/2003 | Mashak |
| 6,828,910 B2 | 12/2004 | VanRyzin et al. |
| 7,305,988 B2 | 12/2007 | Acker et al. |
| 7,762,255 B2 | 7/2010 | Mills |
| 2005/0103338 A1 | 5/2005 | Bunke et al. |
| 2006/0207593 A1 | 9/2006 | Dittmann et al. |
| 2008/0295837 A1* | 12/2008 | McCormick et al. .... 128/204.21 |
| 2009/0133696 A1* | 5/2009 | Remmers et al. ........ 128/204.26 |
| 2010/0292544 A1* | 11/2010 | Sherman et al. ............. 600/300 |
| 2011/0197889 A1* | 8/2011 | Lahde et al. ............. 128/204.28 |

OTHER PUBLICATIONS

Search Report and Written Opinion from corresponding EP Application No. 12150330.4, May 4, 2012.

* cited by examiner

SYSTEM AND METHOD FOR PROVIDING MECHANICAL VENTILATION SUPPORT TO A PATIENT

BACKGROUND

The present disclosure relates to the field of mechanical ventilation for patients undergoing general anesthesia. More specifically, the present disclosure relates to a system and method for controlling the introduction of fresh gas into a breathing circuit.

Mechanical ventilation support is a common therapeutic technique that is provided to a patient that is either too weak from sedation or muscle paralysis to complete a respiratory cycle without external assistance. Artificial ventilation is provided to patient's experiencing total pulmonary failure and is unable to initiate a respiratory cycle under their own power. Ventilatory assistance is provided to patient's that can initiate spontaneous breathing, but benefit from the external control of the volume duration, and inhaled concentrations provided with ventilatory assistance.

Previous mechanical ventilation systems vented expired gases away from the patient and each breath included only fresh gas. Modern mechanical ventilation systems recycle at least a portion of the expired gases from the patient by processing the expired gases and returning them to the patient in a later respiratory cycle. These, low-flow mechanical ventilation systems seek to maximize the use of medical gases delivered to the patient.

BRIEF DISCLOSURE

A system for providing mechanical ventilation support to a patient includes a mechanical ventilator configured to pneumatically provide mechanical ventilation support to the patient. A breathing circuit is pneumatically connected between the mechanical ventilator and a patient connection configured to deliver the mechanical ventilation support to the patient. The breathing circuit comprises an inspiratory limb upstream of the patient connection and an expiratory limb downstream of the patient connection. An inspiratory check valve is disposed within the inspiratory limb of the breathing circuit. A fresh gas manifold is configured to provide fresh gas to the breathing circuit for delivery to the patient. A fresh gas valve is disposed between the fresh gas manifold and the breathing circuit. The fresh gas valve is operable between at least two positions. In a first position, the fresh gas valve directs fresh gas through an upstream conduit that provides the fresh gas to the breathing circuit upstream of the inspiratory check valve. In a second position, the fresh gas valve directs the fresh gas through a downstream conduit that provides the fresh gas to the breathing circuit downstream of the inspiratory check valve. A digital signal processor operates the fresh gas valve selectively between the first position and the second position to provide mechanical ventilation support to the patient.

A method of ventilating a patient with a mechanical ventilator includes operating the mechanical ventilator to provide a series of breaths of ventilatory support to the patient. A flow of fresh gas is introduced into an inspiratory limb of the breathing circuit through a fresh gas flow valve. The flow of fresh gas is delivered continuously to the breathing circuit throughout the series of breaths of ventilatory support delivered to the patient. A ventilatory support value is sensed with at least one gas sensor disposed within the breathing circuit. An operational condition of the breathing circuit is identified with a digital signal processor that receives the sensed ventilatory support value. A fresh gas flow valve is operated with the digital signal processor between a first position and a second position. The first position of the fresh gas flow valve directs the flow of fresh gas into a first conduit that introduces the flow of fresh gas into the inspiratory limb upstream from the inspiratory check valve and the second position directs the flow of fresh gas into a second conduit that introduces the flow of fresh gas into the inspiratory limb downstream from the inspiratory check valve.

A system for providing mechanical ventilation support to a patient includes a breathing circuit pneumatically connected to the patient through a patient connection. A bellows is pneumatically connected to the inspiratory limb and the expiratory limb of the breathing circuit. The bellows receives expired gases from the expiratory limb and releases excess pressure from the breathing circuit through an exhaust valve. The bellows is further connected to a mechanical ventilator that operates the bellows to provide mechanical ventilation support to the patient through the inspiratory limb. An inspiratory check valve is disposed within the inspiratory limb of the breathing circuit. An inspiratory gas sensor is disposed within the inspiratory limb. The inspiratory gas sensor measures a ventilation support value from the inspiratory limb. An expiratory gas sensor is disposed within the expiratory limb. The expiratory gas sensor measures a ventilation support value from the expiratory limb. A fresh gas manifold is configured to provide fresh gas to the breathing circuit for delivery to the patient. A fresh gas valve is disposed between the fresh gas manifold and the breathing circuit. The fresh gas valve is operable between at least two positions. A first position of the fresh gas valve directs fresh gas to an upstream conduit that provides the fresh gas to the breathing circuit upstream of the inspiratory check valve. A second position of the fresh gas valve directs the fresh gas through a downstream conduit that provides the fresh gas to the breathing circuit downstream of the inspiratory check valve. A digital signal processor receives the ventilation support values from the inspiratory gas sensor and the expiratory gas sensor. The digital signal processor determines an operational condition of the breathing circuit from at least one of the ventilation support values and operates the fresh gas valve selectively between the first position and the second position based upon the determined operational condition.

DETAILED DISCLOSURE

Figure 1:
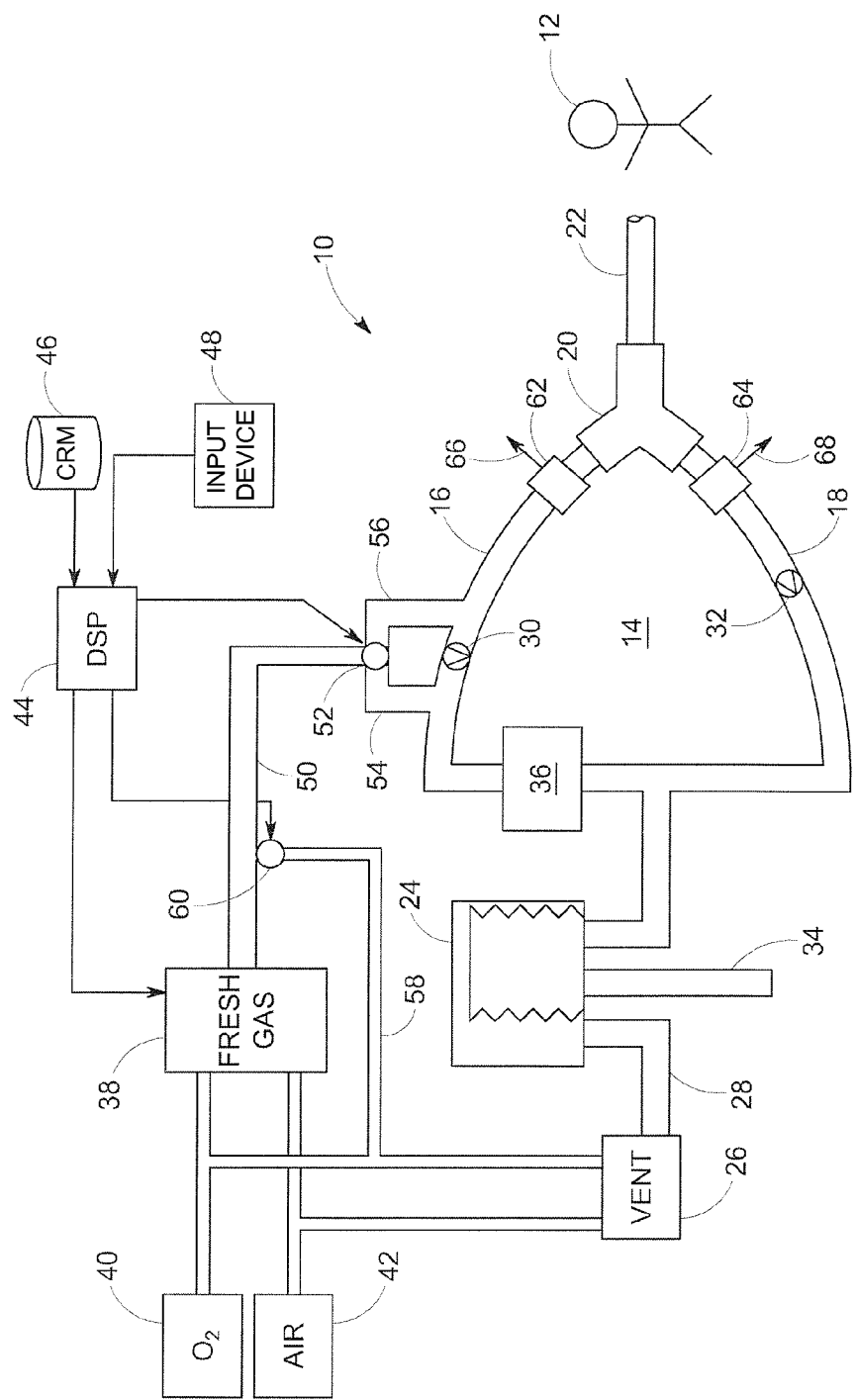
FIG. 1 is a schematic diagram of a system for providing mechanical ventilation support to a patient.

FIG. 1 is a schematic diagram that depicts an embodiment of a system 10 for providing mechanical ventilation support to a patient 12.

The system 10 includes a breathing circuit 14. The breathing circuit 14 directs medical gas towards the patient 12 through an inspiratory limb 16 and directs expired gas away from the patient through an expiratory limb 18. A Y connector 20 connects the inspiratory limb 16 and the expiratory limb 18 to a patient connection 22 that facilitates the pneumatic connection of the system 10 to the patient 12. It is understood that there are a wide variety of patient connections 22 that can be used with embodiments of the system 10. These patient connections 22 includes, but are not limited to, an endotracheal tube, a ventilation mask, and a laryngeal mask.

The breathing circuit 14 is pneumatically connected to a bellows 24. The bellows 24 is operated by a mechanical ventilator 26 that provides a supply of drive gas 28 to the bellows 24 in order to create pressure waveforms of medical gas or breaths within the breathing circuit 14 that are delivered to the patient 12 as respiratory support.

Inspiratory check valve 30 is disposed within the inspiratory limb 16 and expiratory check valve 32 is disposed within the expiratory limb 18. The inspiratory check valve 30 and the expiratory check valve 32 maintain a generally unidirectional flow within the breathing circuit 14. Exceptions to the unidirectional flow within the breathing circuit will be explained in greater detail herein.

In mechanical ventilation support, the system 10 and patient 12 cycle through successive inspiratory and expiratory phases. During an expiratory phase, exhaled gases from the patient 12 are directed from the patient connection 22 into the expiratory limb 18 where the expired gases are further directed into the bellows 24. The mechanical ventilator 26 operates to lower the pressure of the drive gas 28 which allows the bellows 24 to expand to accept the expired breathing gases. Any excess gas volume of expired breathing gases is vented out of the bellows 24 through an exhaust valve 34. When the patient receives artificial ventilation, the size and duration of the expiratory phase and the inspiratory phase are established through control of the mechanical ventilator 26. If the patient 12 is receiving ventilatory assistance, then spontaneous breath attempts by the patient 12 are detected and the mechanical ventilator 26 is operated to provide the programmed ventilatory assistance. During the inspiratory phase, the mechanical ventilator 26 delivers drive gas 28 to the bellows 24, compressing the bellows 24 and forcing the expired gases contained therein out of the bellows 24 and into the inspiratory limb 16. In one embodiment, the gases from the bellows 24 are provided through a carbon dioxide absorber 36 that is located in the flow path of the gases from the bellows 24. The carbon dioxide absorber 36 uses a chemical reaction to trap the carbon dioxide from the expired gases and release oxygen and water. It is understood that in alternative embodiments in addition to the carbon dioxide absorber 36, additional conditioning apparatus may be used to further process the expired gases from the patient for recirculation back to the patient. Such additional conditioning apparatus may include a humidifier, a heat exchanger, filters, or an anesthetic agent source.

Since at least a portion of the expired gases are vented through the exhaust valve 34, a volume of fresh gas must be provided to the inspiratory limb 16 from a fresh gas manifold 38. The fresh gas manifold 38 is connected to sources of medical gas. The sources can include cylinders of pressurized medical gas or wall supply conduits found in a hospital or clinical setting. While an oxygen source 40 and an air source 42 are depicted, it is to be understood that a variety of other medical gases may be used instead of or in addition to oxygen and air. Non-limiting examples of alternative medical gases that can be used include Heliox, nitrous oxide, xenon, or nitrogen (which is used as a balance gas). Additionally, the fresh gas manifold 38 may include an anesthetic vaporizer to dispense vaporized anesthetic agent from an anesthetic liquid reservoir.

A digital signal processor (DSP) 44 is communicatively connected to the fresh gas manifold 38 in order to control the mixture of fresh gases delivered to the inspiratory limb 16. In particular, the DSP 44 operates the fresh gas manifold 38 in order to deliver a specified flow of fresh gas at an established oxygen concentration, as will be disclosed in further detail herein.

The DSP 44 is connected to a computer readable medium 46. The computer readable medium 46 may be any of a variety of known non-volatile readable memory implementations. In one exemplary embodiment, the computer readable medium 46 is flash memory. The computer readable medium 46 can be an integral component (not depicted) of the DSP 44. Alternatively, the computer readable medium 46 can be a separate component that is communicatively connected to the DSP 44.

The computer readable medium 46 is programmed with computer readable code that is accessed and executed by the DSP 44. Upon execution of the computer readable code by the DSP 44, the DSP 44 operates in such a manner as to perform the functions and operations disclosed herein that are attributed to the DSP 44.

An input device 48 is also communicatively connected to the DSP 44. The input device 48 may be a keyboard, soft keys, a touch screen, or a mouse that a clinician uses to enter controlled or operating parameters for the system 10. While not depicted in FIG. 1, the DSP 44 can be communicatively connected to the mechanical ventilator 26, such that the DSP 44 provides commands and controls to the mechanical ventilator 26 such as to operate the mechanical ventilator 26 to provide the functions as described herein.

The bellows 24 is operated by the mechanical ventilator 26 to recirculate expired gases from the patient 12 back to the inspiratory limb 16 for delivery back to the patient 12. Despite gas conditioning, such as provided by the $CO_2$ absorber 36, the volume and constituent gas concentrations in the recirculated gases must be modified through the introduction of fresh gas which is provided from the fresh gas manifold 38 through a fresh gas conduit 50. The fresh gas conduit 50 splits into an upstream conduit 54 that is fluidly connected to the inspiratory limb 16 at a location upstream from the inspiratory check valve 30. The fresh gas conduit 50 also splits into a downstream conduit 56 that fluidly connects to the inspiratory limb 16 at a location downstream from the inspiratory check valve 30. One or more gas sensors (not depicted) monitor at least one of pressure, volume, flow rate, and constituent gas concentrations of the recirculated breathing gases. The DSP 44 receives these monitored values and controls the fresh gas manifold 38 to supply a combination of fresh gases through the fresh gas conduit 50 such that the breathing gases supplied to the patient 12 meet a desired volume, and constituent gas concentration requirements. A fresh gas valve 52 is at least a three-way-valve that connects the fresh gas conduit 50, the upstream conduit 54, and the downstream conduit 56. The fresh gas valve 52 is operated by the DSP 44 such as to define two alternative flow paths, a first flow path wherein the fresh gases are provided through the fresh gas conduit 50 and the upstream conduit 54 to be provided to the inspiratory limb 16 at a location above the inspiratory check valve 30. The DSP 44 further operates the fresh gas valve 52 to a second position wherein the fresh gases provided by the fresh gas manifold 38 through the fresh gas conduit 50 and the downstream conduit 56 to be provided to the inspiratory limb 16 at a location downstream of the inspiratory check valve 30.

One operational feature of the system 10 is the ability to provide an oxygen flush procedure. In an oxygen flush, 100% oxygen is flowed from the fresh gas manifold 38 through the breathing circuit 14 at a high flow rate. This procedure may be used to selectively provide the patient 12 with a period of high oxygen concentration ventilation or rapidly refill the gas volume in the bellows. Alternatively, such a procedure may be used to rapidly reduce high concentrations of anesthetic agent in the breathing circuit 14 and the patient 12. In the system 10, an oxygen flush conduit 58 fluidly connects the oxygen source 40 to the fresh gas conduit 50. An oxygen flush valve 60 is disposed within the fresh gas conduit 58. The oxygen flush valve 60 is operated to deliver a high flow of mostly oxygen to the fresh gas line 50. In embodiments, oxygen flush valve 60 is a mechanically actuated by a momentary push valve and the actuation or the flow of oxygen flush is sensed and communicated to the DSP 44

In an alternative embodiment, the flush valve 60 is operated by the DSP 44 to deliver the high flow of oxygen. The DSP 44 initiates an oxygen flush procedure upon receiving a control signal from the input device 48 that is indicative of a clinician making a specific selection to initiate an oxygen flush procedure. In one arrangement, the fresh gas valve 52 is more than a three-way-valve or is in effect a plurality of valves such that the oxygen flush conduit 58 connects directly to the fresh gas valve 52 (not depicted) and the flow of oxygen gas during an oxygen flush procedure completely bypasses the fresh gas conduit 50. In this embodiment, the fresh gas valve is operated to not only select the destination of the gas flow (upstream conduit 54 or downstream conduit 56), but also the source of the gas flow (fresh gas conduit 50 or oxygen flush conduit 58).

An inspiratory gas sensor 62 is disposed in the inspiratory limb 16 and an expiratory gas sensor 64 is disposed within the expiratory limb 18. The inspiratory gas sensor 62 and the expiratory gas sensor 64 each sense at least one ventilatory support value. Examples of ventilatory support values include pressure, flow rate, and constituent gas concentration at the sensor. The inspiratory gas sensor 62 and expiratory gas sensor 64 provides the DSP 44 with signals indicative of these ventilatory support values from the medical gas delivered to the patient 66 and signals representative of ventilatory support values from the gases exhaled by the patient 68.

The DSP 44 receives these ventilatory support values that exemplarily include inspiratory flow rate, inspiratory pressure, inspiratory oxygen concentration, expiratory flow rate, expiratory pressure, and expiratory oxygen concentration. In some embodiments sensors 62 and 64 may be combined into a single sensor (not shown) and can be located at the patient connection 22 to sense the inspired signal 66 and the expired signal 68 during the corresponding inspiration and expiration phase of the ventilation. It will be recognized by a person of ordinary skill in the art that alternative embodiments may include some or all of these ventilatory support values or would recognize other values that may also be used. The DSP 44 processes these values in order to identify an operational condition of the breathing circuit, as will be disclosed in further herein. The DSP 44 controls the fresh gas valve 52 such that the fresh gas is provided to the inspiratory limb 16 at an optimal position with respect to the inspiratory check valve 30 based upon the identified operational condition of the breathing circuit 14.

Reference is made herein to FIGS. 2A, 2B, 3A, and 3B which each depict the flow paths taken by medical gases under different conditions within the system. FIGS. 2A-3B depict a simplified embodiment of the system 10; however, it is to be understood that in alternative embodiments, the more detailed features shown in FIG. 1 would also be present. Like reference numerals have been used in FIGS. 1-3B to denote like structures between the figures.

Figure 2A:
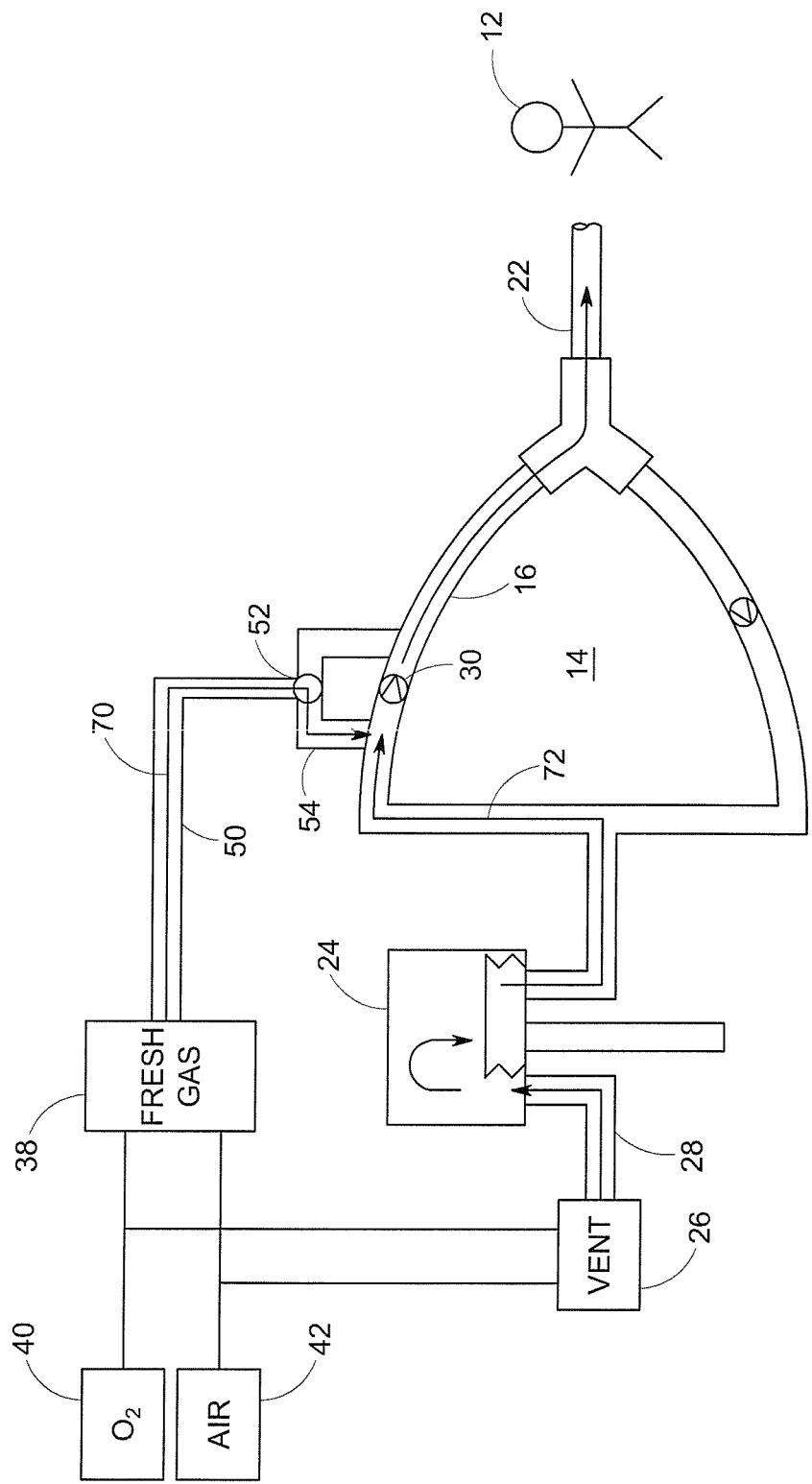
FIG. 2A is a schematic diagram that depicts fresh gas delivery upstream of the inspiratory check valve during inspiration.
Figure 2B:
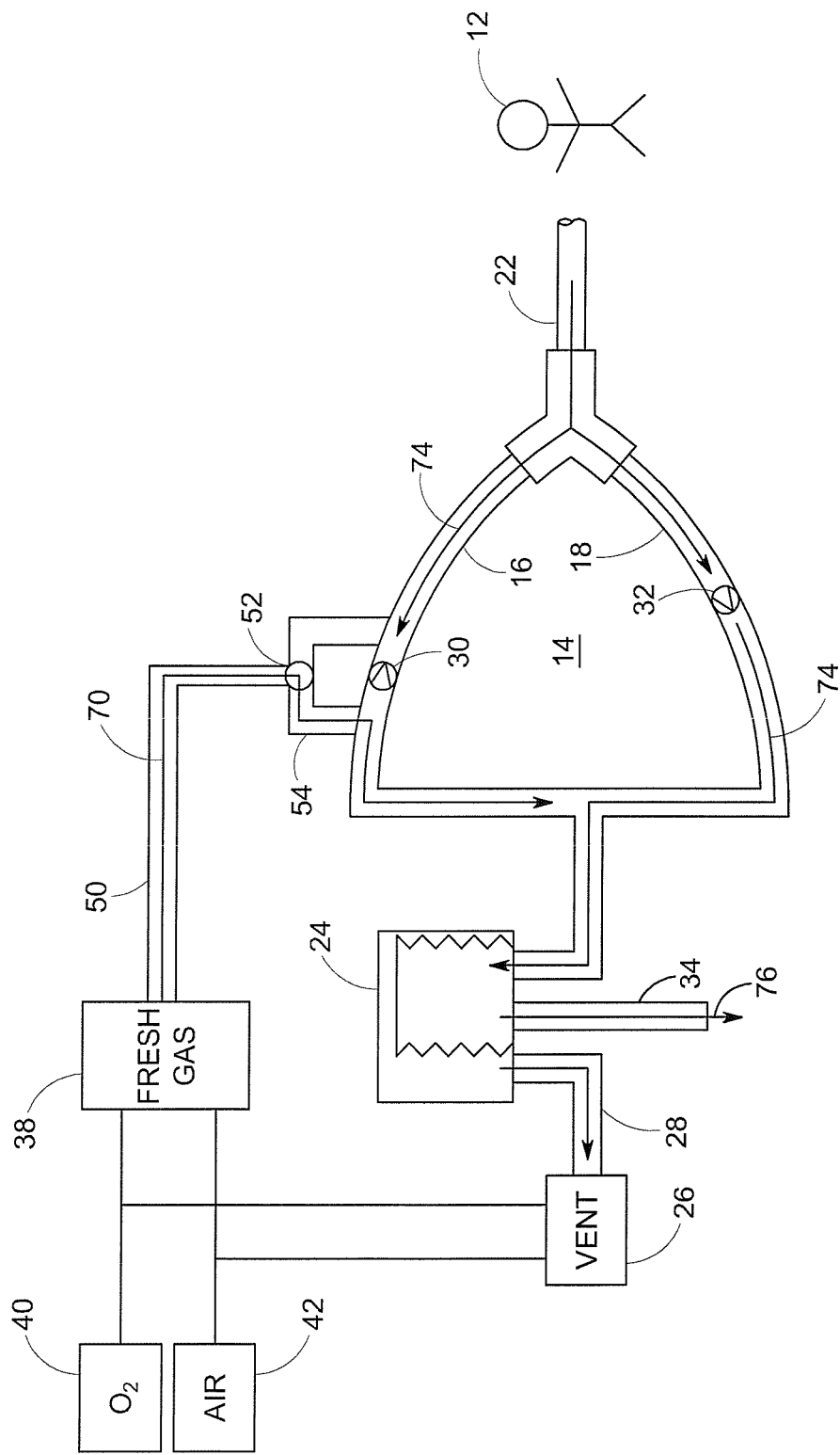
FIG. 2B is a schematic diagram that depicts fresh gas delivery upstream of the inspiratory check valve during expiration.

FIGS. 2A and 2B depict the flow of medical gas when the fresh gas valve 52 is operated in the first position such that a flow of fresh gas 70 is delivered through the upstream conduit 54 upstream of the inspiratory check valve 30. FIG. 2A depicts an inspiratory phase of the respiratory cycle with this configuration of the fresh gas valve 52. The mechanical ventilator 26 uses one or more of the oxygen and air, respectively, from oxygen source 40 and air source 42 as a drive gas 28 that is directed into the bellows 24. It is understood that in alternative embodiments, the mechanical ventilator 26 includes its own source of drive gas, which exemplarily may be a compressor (not depicted) or the bellows 24 can be electrically driven such as by a motor or solenoid (not depicted). The drive gas 28 compresses the bellows 24 and forces the medical gas flow 72 out of the bellows 24 into the inspiratory limb 16 of the breathing circuit 14. The fresh gas flow 70 provided by the fresh gas manifold 38 flows through the fresh gas conduit 50 and the upstream conduit 54 to join the medical gas flow 72 from the bellows 24 before going through the inspiratory check valve 30, the inspiratory limb 16 and the patient connection 22 to be delivered to the patient 12.

FIG. 2B depicts the gas flow during an expiratory phase of the respiratory cycle with the fresh gas valve 52 operated in the first position to direct the flow of fresh gas 70 through the flow of the upstream conduit 54.

During expiration by the patient 12, expired gases 74 flow back through the patient connection 22 into the breathing circuit 14. As can be seen in FIG. 2B, a portion of the expired gas flow 74 is directed into a portion of the inspiratory limb 16, but further flow is prevented by inspiratory check valve 30. The majority of the expired gas flow 74 is directed through the expiratory limb 18 and allowed to pass through the expiratory check valve 32. The expired gas flow 74 that passes through the expiratory check valve 32 is directed into the bellows 24. During the expiratory phase, the mechanical ventilator 26 is operated to reduce the pressure of the drive gas 28 to below that of the pressure of the expired gases 74 in the breathing circuit 14. Therefore, as the bellows 24 expands, the drive gas 28 is forced out. This creates a volume within the bellows 24 to receive the expired gas flow 74. Any excess expired gases beyond the volume contained within the bellows 24 are removed through an exhaust valve 34 as an exhausted gas 76.

The fresh gas manifold 38 is operated to continuously provide the fresh gas flow 70. However, due to the pressure in the inspiratory limb 16 downstream of the inspiratory check valve 30 caused by the expired gases 74, the fresh gas flow 70 is directed upstream to combine with the expired gas flow and enter the bellows 24. As the expired gas flow 74 represents a larger volume of gas, the addition of the fresh gas flow 70 into the bellows 24 will cause a portion of the expired gas flow 74 to be directed through the exhaust valve 34 as exhausted gas flow 76.

Figure 3A:
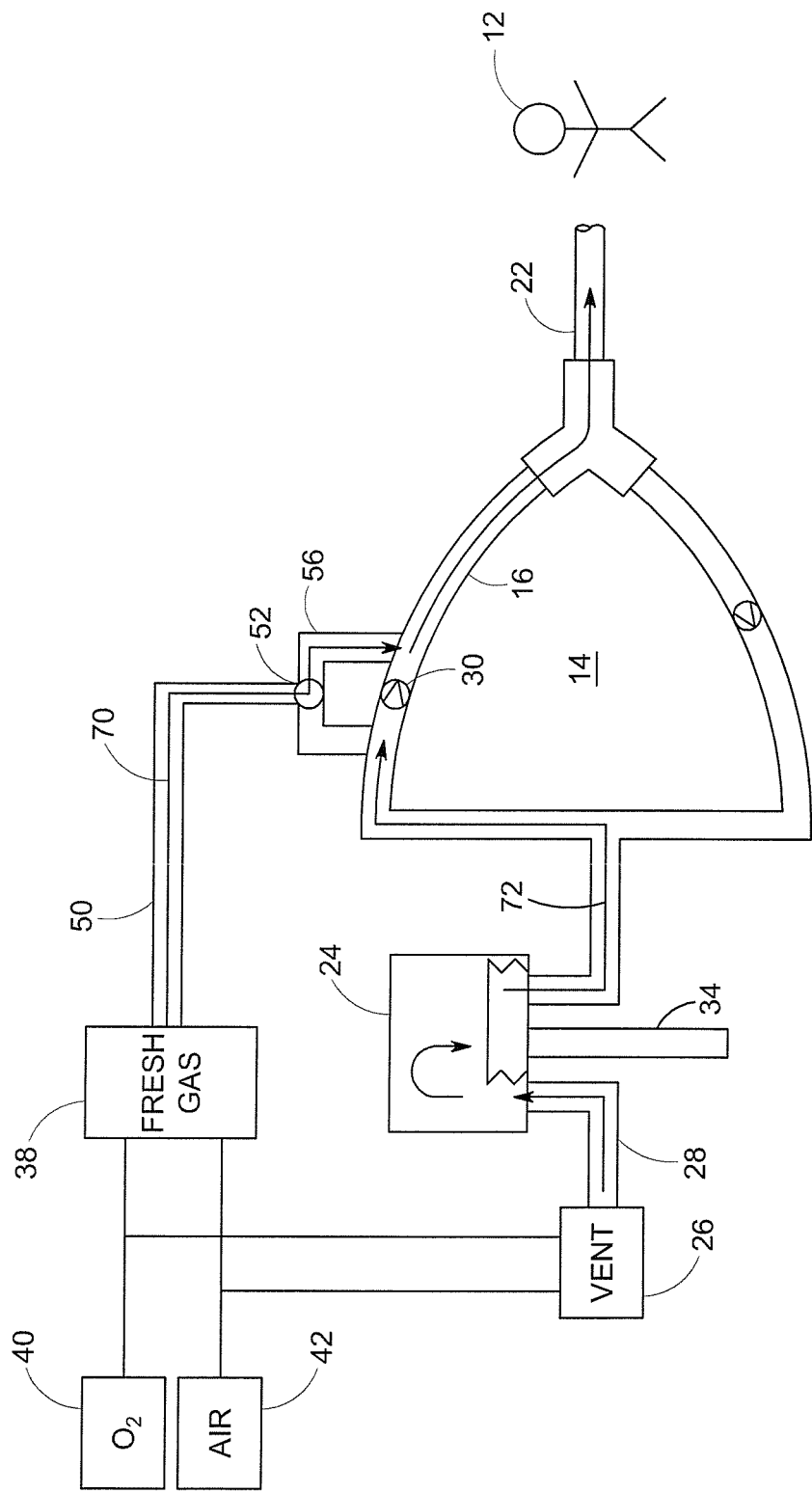
FIG. 3A is a schematic diagram that depicts fresh gas delivery downstream of the inspiratory check valve during patient inspiration.

FIG. 3A depicts the flow of gases in an embodiment of the system wherein the fresh gas valve 52 is operated in the second position such that the fresh gas flow 70 from the fresh gas manifold 38 is directed through the fresh gas conduit 50 and the downstream conduit 56 into the inspiratory limb 16 of the breathing circuit 14 at a location downstream of the inspiratory check valve 30. FIG. 3A depicts the operation of this embodiment during an inspiratory phase of the respiratory cycle by the patient 12.

The mechanical ventilator 26 provides drive gas 28 to the bellows 24 which compresses the bellows to deliver a medical gas flow 72 into the inspiratory limb 16 of the breathing circuit 14. The medical gas flow 72 proceeds through the inspiratory check valve 30 where the medical gas flow 72 combines with the fresh gas flow 70 for delivery to the patient 12 through the patient connection 22.

Figure 3B:
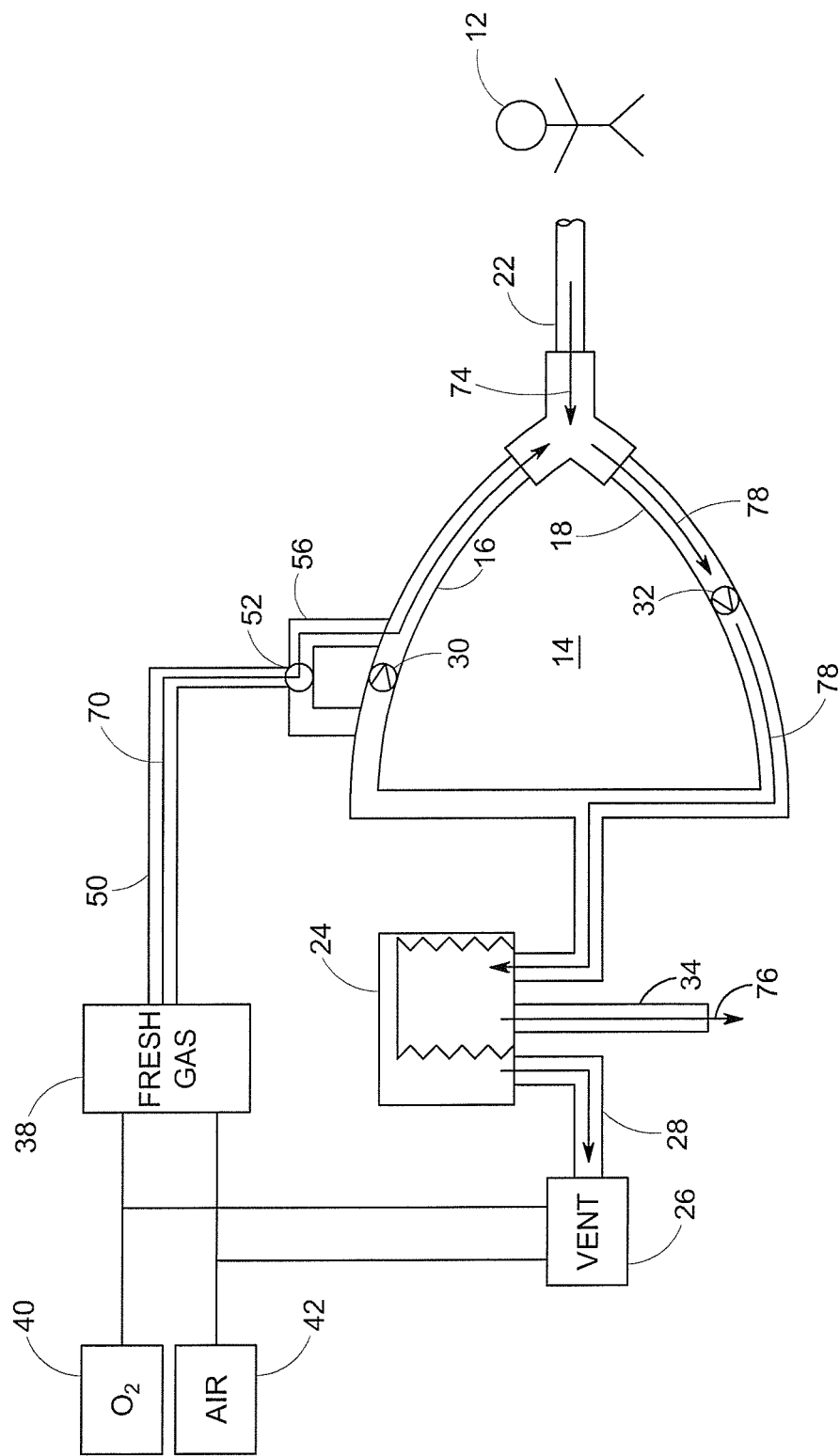
FIG. 3B is a schematic diagram that depicts fresh gas delivery downstream of the inspiratory check valve during patient expiration.

FIG. 3B depicts the flow of gas in a configuration of the system when the fresh gas valve 52 is operated in the second condition such that the flow of fresh gas 70 is delivered to the inspiratory limb 16 at a location downstream of the inspiratory check valve 30.

In FIG. 3B, the expired gases 74 leave the patient 12 through the patient connection 22 and combine with the fresh gas flow 70 in the breathing circuit 14 from the inspiratory limb 16. A combined gas flow 78 of expired gas and fresh gas flows through the expiratory limb 18 and the expiratory check valve 32. The combined gas flow 78 is further directed through the breathing circuit 14 into the bellows 24 wherein the bellows 24 expands to receive the volume of the combined gas flow 78. Any excess gas flow received in the bellows 24 is exhausted as exhaust gas flow 76 through an exhaust valve 34.

With reference to FIGS. 1-3B, the control of the fresh gas valve 52 by the DSP 44 provides a system 10 wherein the delivery of the fresh gas flow 70 is selected for an optimal position with respect to the inspiratory check valve 30 based upon a sensed condition within the breathing circuit 14 or the overall system 10.

With specific reference to FIG. 2B, it can be seen that the expired gas flow 74 forms the majority of the gas that is provided to the bellows 24. Therefore, the continuous fresh gas flow 70 enters the bellows 24 and a portion of the expired gas flow 74 is vented out of the bellows 24 as an exhausted gas flow 76. Therefore, operation of the fresh gas valve 52 in the first position presents an advantage of conserving the fresh gas introduced into the system during an expiratory phase of the patient's respiration system. This is contrasted with the gas flows found in FIG. 3B, wherein the combined gas flow 78 is provided into the bellows 24. As the combined gas flow 78 comprises the fresh gas flow 70 and the expired gas flow 74, during pauses at the beginning or end of a patient expiration, the newly introduced fresh gas flow 70 circles through the breathing circuit 14 and into the bellows 24 wherein the fresh gas flow 70 is ultimately vented as exhausted gas flow 76 through the exhaust valve 34. Therefore, during an expiratory phase of the system 10 when the fresh gas valve 52 is operated in the second position, unused fresh gas can be wasted through ventilation to the ambient atmosphere or another form of gas scavenger.

In a further exemplarily embodiment, in FIG. 2B, the expired gases 74 flow into the inspiratory limb 16 until this flow is stopped by inspiratory check valve 30. Therefore, when the system cycles over to an inspiratory phase as shown in FIG. 2A, the first gas delivered to the patient 12 is the expired gas that had been previously trapped in the inspiratory limb 16. While the exact volume of expired gas contained within the inspiratory limb 16 downstream of the inspiratory check valve 30 can be relatively small, this feature can introduce errors in the gas concentrations actually delivered to the patient 12, particularly if the patient is experiencing low tidal volumes, exemplarily 50 milliliters or less.

The example found in FIGS. 2A and 2B is to be contrasted with that shown in FIGS. 3A and 3B. When the fresh gas valve 52 is operated in the second position, the fresh gas flow 70 flows through the inspiratory limb 16 during an expiratory phase of the patient as shown in FIG. 3B. Therefore, when the patient 12 cycles into an inspiratory phase, the inspiratory limb 16 is filled with the fresh gas flow 70 and the patient 12 is first provided with this fresh gas.

Figure 4:
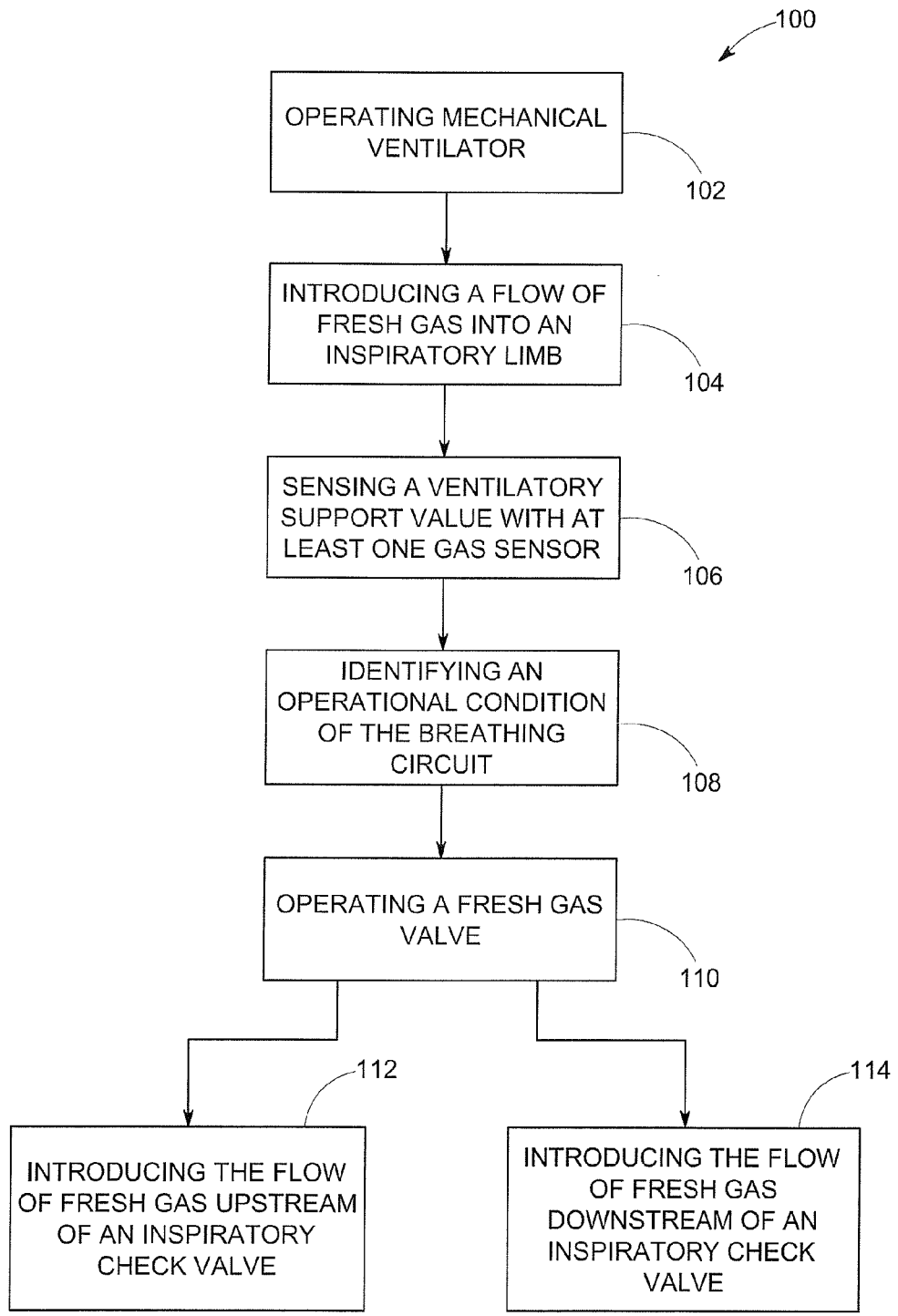
FIG. 4 is a flow chart that depicts an embodiment of a method of ventilating a patient with a mechanical ventilator.

Additional features of the system will be described in greater detail herein with respect to the flow chart of FIG. 4. FIG. 4 is a flow chart that depicts an embodiment of a method 100 of ventilating a patient with a mechanical ventilator. At 102, a mechanical ventilator is operated in order to provide a series of fluid waveforms or breaths that provide ventilatory support to the patient.

At 104, a flow of fresh gas is introduced into an inspiratory limb of a breathing circuit that is mechanically connected to the patient. The flow of fresh gas is introduced into the inspiratory limb through a fresh gas flow valve.

Next, at 106, at least one ventilatory support value is sensed with at least one gas sensor. In an embodiment, the at least one gas sensor includes one or both of the inspiratory gas sensor 62 and the expiratory gas sensor 64 depicted in FIG. 1. The at least one gas sensor senses any of a variety of ventilatory support values, which include, but are not limited to inspiratory flow rate, inspiratory pressure, inspiratory oxygen concentration, expiratory flow rate, expiratory pressure, and expiratory oxygen concentration. It will be recognized by a person of ordinary skill in the art that alternative ventilatory support values are sensed by the at least one sensor. The at least one sensor provides the sensed at least one ventilatory support value to a digital signal processor that is communicatively connected to the fresh gas valve.

At 108, the digital signal processor identifies an operational condition of the breathing circuit by analyzing at least one of the at least one ventilatory support values received from the at least one gas sensor in 106. The identified operational condition of the breathing circuit may take a variety of forms which dictate an operational response by the digital signal processor.

The following are a few non-limiting examples of operational conditions of the breathing circuit that may be identified by the digital signal processor. Measurements obtained from the inspiratory gas sensor can be used by the digital signal processor to determine the tidal volume of the patient's respiration. If the tidal volume is small, exemplarily less than 200 milliliters, then the digital signal processor can identify that the patient is either an infant or otherwise has a similarly small tidal volume such that the expired gases trapped in the inspiratory limb may effect the quality of the respiratory support provided to the patient.

In an alternative embodiment, the inspiratory gas sensor can measure a flow rate and/or oxygen concentration in the inspiratory limb and identify that an oxygen flush procedure has been initiated. Typically, a oxygen flush procedure will have a flow between 35 liters per minute and 70 liters per minute of pure or substantially pure oxygen.

It is also understood that in alternative embodiments, the digital signal processor 44 may receive an input, such as from input device 48 that will dictate the operational condition of the breathing circuit. Such examples may be an initiation of an "infant" ventilation setting, a low tidal volume setting, or the selection of an input to initiate an oxygen flush procedure. In these embodiments, the ventilatory support value sensed by the inspiratory gas sensor can be used to confirm that the identified command is being followed by the ventilation support system.

A still further operational condition of the breathing circuit that can be identified by the digital signal processor is that of a blocked expiratory limb. A blocked expiratory limb causes increased risks to the patient for barotrauma as the expired gas flow is not removed from the breathing circuit and additional gas is delivered to the patient's lung which can inappropriately deliver too great of a pressure or volume of gas to the patient's lungs, thus resulting in damage to the lungs themselves. Ventilatory support values sensed by the expiratory gas sensor can be used in identifying a blockage of the expiratory limb. One or more of the following characteristics in the ventilatory support values may result in the digital signal processor identifying that the expiratory limb is blocked. These characteristics include a sustained high airway pressure in the patient, an increasing airway pressure at the end of patient expiration, and a decrease in gas flow through the expiratory limb.

Therefore, three exemplary operational conditions of the breathing circuit have been disclosed, including low tidal volume, oxygen flush procedures, and a blocked expiratory limb. However, a person of ordinary skill in the art will recognize other operational conditions that may similarly be identified by the digital signal processor 44.

At 110, the digital signal processor operates the fresh gas valve 52 in response to the identified operational condition. At 112, the digital signal processor operates the fresh gas valve into the first position to introduce the flow of fresh gas upstream of the inspiratory check valve. The introduction of the flow of fresh gas upstream of the inspiratory check valve at 112, can be initiated by the digital signal processor upon identifying that the expiratory limb is blocked or that an oxygen flush procedure has been initiated. In both of those operational conditions of the breathing circuit, introduction of the fresh gas flow upstream of the inspiratory check valve is preferred as the patient is protected from barotrauma risk as excess fresh gas flows will be vented out through the exhaust vent 34, rather than delivered directly to the patient 12.

Alternatively, at 114, the DSP operates the fresh gas valve to introduce the flow of fresh gas downstream of the inspiratory check valve. This operation of the fresh gas valve is initiated by the digital signal processor in response to identifying that a low tidal volume is being supplied to the patient. Due to the low tidal volume, the introduction of the fresh gas flow downstream of the inspiratory check valve flushes the inspiratory limb of expired gases such that the fresh gas flow is delivered to the patient from the start of inspiration, rather than the patient initially receiving expired gases. Alternatively, the clinician can select (via the input device 48 through the DSP 44 that controls the fresh gas valve 52) the entry of the fresh gas into the breathing circuit 14 based on clinical needs such as a rapid change in the gas concentrations inhaled by the patient 12.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for providing mechanical ventilation support to a patient, the system comprising:
    a mechanical ventilator configured to pneumatically provide mechanical ventilation support to the patient;
    a breathing circuit pneumatically connected between the mechanical ventilator and a patient connection configured to deliver the mechanical ventilation support to the patient, wherein the breathing circuit comprises an inspiratory limb upstream of the patient connection and an expiratory limb downstream of the patient connection;
    an inspiratory check valve disposed within the inspiratory limb of the breathing circuit;
    a fresh gas manifold configured to provide fresh gas to the breathing circuit for delivery to the patient;
    a fresh gas valve disposed between the fresh gas manifold and the breathing circuit, the fresh gas valve being operable between at least two positions, wherein in a first position the fresh gas valve directs fresh gas through an upstream conduit that provides the fresh gas to the breathing circuit upstream of the inspiratory check valve, and in a second position the fresh gas valve directs the fresh gas through a downstream conduit that provides the fresh gas to the breathing circuit downstream of the inspiratory check valve; and
    a digital signal processor that operates the fresh gas valve selectively between the first position and the second position to provide mechanical ventilation support to the patient;
    wherein the inspiratory limb and the expiratory limb are fluidly connected downstream of the patient and wherein when the fresh gas valve is in the second position fresh gas combines with the expired gas from the expiratory limb downstream of an expiratory check valve.

2. The system of claim 1, further comprising:
    an inspiratory gas sensor disposed within the inspiratory limb, the inspiratory gas sensor communicatively connected to the digital signal processor; and
    an expiratory gas sensor disposed within the expiratory limb, the expiratory gas sensor communicatively connected to the digital signal processor;
    wherein the digital signal processor monitors a condition of the delivery of mechanical ventilation support to the patient and operates the fresh gas salve between the first position and the second position based upon the condition.

3. The system of claim 2, wherein the digital signal processor identifies a blockage in the expiratory limb and the digital signal processor operates the fresh gas valve to the first position.

4. The system of claim 2, wherein the digital signal processor identifies that the patient is receiving ventilation at a low tidal volume and the digital signal processor operates the fresh gas valve to the second position.

5. The system of claim 1, wherein operation in the first position minimizes a loss of medical gas from the system.

6. The system of claim 1, wherein operation in the second position maximizes the delivery of medical gas to the patient.

7. The system of claim 1 further comprising a bellows operated by the mechanical ventilator, the bellows being pneumatically connected to the breathing circuit and receiving expired gases from the expiratory limb of the breathing circuit.

8. The system of claim 7, further comprising a carbon dioxide absorber pneumatically connected in the breathing circuit, downstream from the bellows and upstream from the inspiratory check valve.

9. The system of claim 7, wherein the bellows further comprises an exhaust valve, wherein excess pressure within the breathing circuit is released through the exhaust valve.

10. The system of claim 9, further comprising:
    an oxygen flush conduit that is selectively fluidly connected to the breathing circuit through the fresh gas valve, a flow of oxygen gas in the oxygen flush conduit being selectively controlled by the digital signal processor;

wherein the digital signal processor operates the fresh gas valve in the first position when the flow of oxygen gas in the oxygen flush conduit is selectively initiated.

11. A method of ventilating a patient with a mechanical ventilator pneumatically connected to the patient through a breathing circuit with an inspiratory check valve and a patient connection, the method comprising:
   operating the mechanical ventilator to provide a series of breaths of ventilatory support to the patient;
   introducing a flow of fresh gas into an inspiratory limb of the breathing circuit through a fresh gas valve, the flow of fresh gas being delivered to the patient in the series of breaths of ventilatory support;
   sensing a ventilatory support value with at least one gas sensor disposed within the breathing circuit;
   identifying an operational condition of the breathing circuit with a digital signal processor that receives the sensed ventilatory support value;
   operating the fresh gas valve with the digital signal processor between a first position and a second position, wherein the first position directs the flow of fresh gas into a first conduit that introduces the flow of fresh gas into the inspiratory limb upstream from the inspiratory check valve and the second position directs the flow of fresh gas into a second conduit that introduces the flow of fresh gas into the inspiratory limb downstream from the inspiratory check valve;
   and recirculating expired gases to the patient by fluidly connecting an expiratory limb of the breathing circuit having an expiratory check valve to the inspiratory limb wherein when the fresh gas valve is in the second position the flow of fresh gas combines with the expired gases downstream of the expiratory check valve.

12. The method of claim 11, further comprising:
   wherein the expired gases are further recirculated to the patient by fluidly connecting the expiratory limb of the breathing circuit to a bellows of the mechanical ventilator;
   exhausting any excess gasses in the bellows through an exhaust port during an expiratory phase of an operation of the mechanical ventilator.

13. The method of claim 12, further comprising:
   identifying the operational condition of the breathing circuit as delivering a low tidal volume; and
   operating the fresh gas valve to the second position.

14. The method of claim 12, further comprising:
   identifying the operational condition of the breathing circuit as having a blocked expiratory limb; and
   operating the fresh gas valve to the first position.

15. The method of claim 11, further comprising:
   receiving, with the digital signal processor, an initiation of an oxygen flush procedure;
   identifying, with the digital signal processor, that the operational condition of the breathing circuit as performing an oxygen flush;
   operating the fresh gas valve to the first position with the digital signal processor; and
   delivering an oxygen flush through the fresh gas valve.

16. A system for providing mechanical ventilation support to a patient, the system comprising:
   a breathing circuit pneumatically connected to the patient through a patient connection configured to deliver the mechanical ventilation support to the patient, wherein the breathing circuit comprises an inspiratory limb upstream of the patient connection and an expiratory limb downstream of the patient connection;
   a bellows pneumatically connected to the inspiratory limb and the expiratory limb of the breathing circuit, the bellows receives expired gases from the expiratory limb and releases excess pressure from the breathing circuit through an exhaust valve, the bellows further being connected to a mechanical ventilator that operates the bellows to provide mechanical ventilation support to the patient through the inspiratory limb;
   an inspiratory check valve disposed within the inspiratory limb of the breathing circuit;
   at least one gas sensor disposed within the breathing circuit, the at least one gas sensor measures a ventilation support value from the gases in the breathing circuit;
   a fresh gas manifold configured to provide fresh gas to the breathing circuit for delivery to the patient;
   a fresh gas valve disposed between the fresh gas manifold and the breathing circuit, the fresh gas valve being operable between at least two positions, wherein in a first position the fresh gas valve directs fresh gas through an upstream conduit that provides the fresh gas to the breathing circuit upstream of the inspiratory check valve, and in a second position the fresh gas valve directs the fresh gas through a downstream conduit that provides the fresh gas to the breathing circuit downstream of the inspiratory check valve;
   a digital signal processor that receives the at least one ventilation support value from the at least one gas sensor, the digital signal processor determines an operational condition of the breathing circuit from at least one of the ventilation support values and operates the fresh gas valve selectively between the first position and the second position based upon the determined operational condition.

17. The system of claim 16, further comprising:
   an oxygen flush conduit that is connected to the breathing circuit through the fresh gas valve, a flow of oxygen gas in the oxygen flush conduit being detected or controlled by the digital signal processor;
   wherein when the digital signal processor detects or controls the flow of oxygen in the oxygen flush conduit and operates the fresh gas valve in the first position.

18. The system of claim 16, wherein the at least one gas sensor measures a low tidal volume as the ventilation support value; and
   wherein the digital signal processor determines that the operational condition is a low tidal volume and the digital signal processor operates the fresh gas valve in the second position.

19. The system of claim 16, wherein the at least one gas sensor measures at least one of sustained high airway pressure, increasing airway pressure at an end of an expiratory phase, and a decrease in gas flow through the expiratory limb;
   wherein the digital signal processor determines that the operational condition is a blocked expiratory limb and the digital signal processor operates the fresh gas valve in the first position.

20. The system of claim 19, wherein operation of the fresh gas valve in the first position reduces wasted fresh gas as expired gases from the patient are exhausted from the bellows before the fresh gas.

* * * * *